(12) United States Patent
Guma

(10) Patent No.: US 7,168,101 B2
(45) Date of Patent: Jan. 30, 2007

(54) SECURITY UNDERWEAR DEVICE FOR SEXUAL ORGANS

(76) Inventor: Tesfa Guma, 7709 Newcastle Dr., Annandale, VA (US) 22003

( * ) Notice: Subject to any disclaimer, the term of this patent is extended or adjusted under 35 U.S.C. 154(b) by 0 days.

(21) Appl. No.: 11/056,988

(22) Filed: Feb. 14, 2005

(65) Prior Publication Data

US 2006/0179552 A1 Aug. 17, 2006

(51) Int. Cl.
*A41B 9/04* (2006.01)

(52) U.S. Cl. .................. 2/408; 2/406; 2/466; 450/100; 450/114

(58) Field of Classification Search .................. 2/406, 2/408, 466; 450/100, 110; 405/100, 114
See application file for complete search history.

(56) References Cited

U.S. PATENT DOCUMENTS

| 33,162 | A | * | 8/1861 | Reynolds | 128/883 |
|---|---|---|---|---|---|
| 875,845 | A | * | 1/1908 | Perkins | 128/883 |
| 1,971,558 | A | * | 8/1934 | Goodman | 604/394 |
| 3,339,208 | A | * | 9/1967 | Marbach | 2/67 |
| 3,397,697 | A | * | 8/1968 | Rickard | 604/370 |
| 4,637,078 | A | * | 1/1987 | Southwell | 2/408 |
| 4,922,899 | A | * | 5/1990 | Graff et al. | 602/72 |
| 5,368,050 | A | * | 11/1994 | Donelan | 128/884 |
| 5,483,705 | A | * | 1/1996 | DiMatteo | 2/466 |
| 5,485,636 | A | * | 1/1996 | Yandell | 2/406 |
| 5,613,251 | A | * | 3/1997 | Yandell | 2/338 |
| 5,636,387 | A | * | 6/1997 | Lundy | 2/408 |
| 2003/0056789 | A1 | * | 3/2003 | Takano et al. | 128/203.12 |

FOREIGN PATENT DOCUMENTS

GB 2227643 * 4/1989

* cited by examiner

*Primary Examiner*—Gary L. Welch
*Assistant Examiner*—Richale L. Haney
(74) *Attorney, Agent, or Firm*—Tesfa Guma

(57) ABSTRACT

Security underwear is a protective cover for female genital and anal opening against illicit sex and risk of contracting venereal diseases. It is made up of a unit for the genital which has an opening for urine passage and another unit for anal opening which allows free passage of stool. The cover for the genital is further composed of urine receiving channel and flaps to cover the said opening. The cover for anal opening has a lid which is hinged to a frame around anal opening which is in turn fastened to the back side portion of the belt. The two units are connected at the crotch. The channel, the flap and the lid, each opens and closes on its own by spring action. This enables the wearer to urinate and pass stool without taking off the protective covers. The unit for the genital can be worn either in combination with the anal cover or without it. In deployment the unit for genital cover is fastened by a strap to the front portion of the belt. All components of the device are made of materials very hard to cut or break. Padding is used to make the protective cover comfortable to wear.

9 Claims, 3 Drawing Sheets

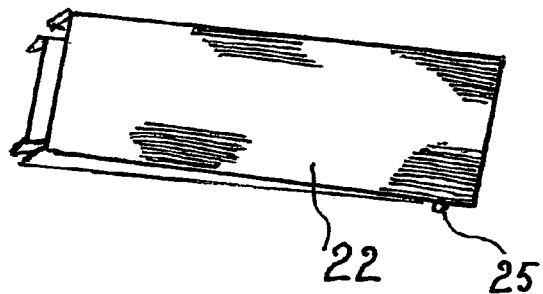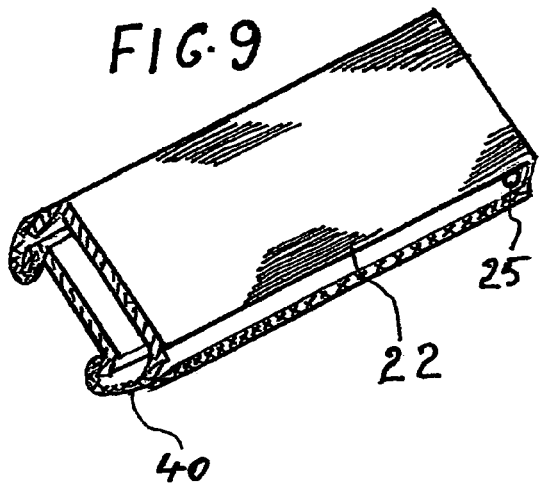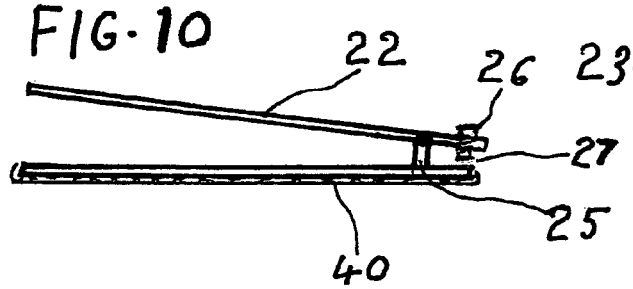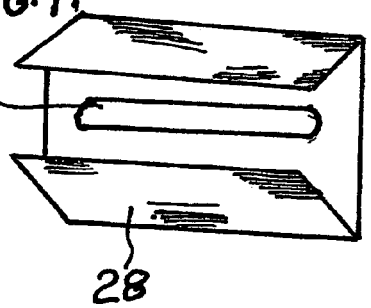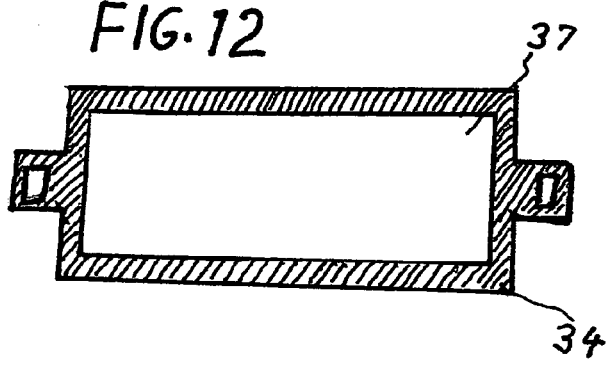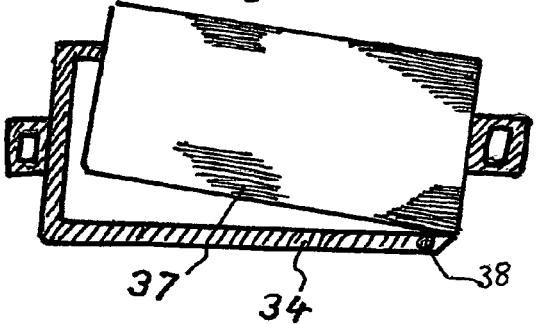

SECURITY UNDERWEAR DEVICE FOR SEXUAL ORGANS

BACKGROUND OF THE INVENTION

Venereal diseases such as syphilis, herpes, gonorrhea and most importantly AIDS, have been the major causes of sufferings and deaths of millions of people world wide. In addition, the consequential psychological, social and economic damages have caused unparalleled catastrophe. These diseases are mostly transmitted during sexual contacts. In other words they are transmitted via sexual organs when the two come in contact, be it by consensual sex or illicit sex. The transmittal of venereal diseases are also caused by the flow of associated fluids discharged from one uncovered genitalia to another unprotected sexual organ. One of the most affected groups who practice illicit sex are school age children. Rape is also a violent universal means of defying a person of his or her human dignity, psychological depravation and moral damage. Stopping the spread of AIDS/HIV virus and empowerment of sex victims is the main objective of this invention.

REFERENCES CITED

U.S. Patent Documents:
1/1908 Perkins U.S. Pat. No. 875,845
7/1986 Bouwhuis U.S. Pat. No. 4,599,751
11/1994 Donelan U.S. Pat. No. 5,368,050
3/1997 Yadell U.S. Pat. No. 5,613,251

U.S. Pat. No. 875,845 issued Jan. 7, 1908 to E. E. Perkins discloses a sexual armor comprising a rigid arch plate applied in the crotch thereof, with a segmental central slot, having a gate to open and close the slot and a lock to secure the device in position. This device allows urine to be splattered rather than the normal flow. Further more, the device is positioned flat against the opening of the genital. Such direct contact of the device with the perforated surface flatly placed against the opening of the genital would allow sexual discharge, i.e. in the case of external ejaculation, even without penetration, to flow into the opening of the organ and enable the transmittal of the disease, thus infecting the person. Further more this device does not teach a method of fully using the toilet, especially to pass stool, without taking off the sexual armor. U.S. Pat. No. 4,599,751 issued Jul. 15, 1986 to H. E Bouwhuis discloses a chain mail pants with close fitting legs and a lockable belt for this purpose. This would have to be custom fitted so that access cannot be attained by pushing the garment aside at the legs. It would also be quite confining and uncomfortable. The main drawback of this device is that it does not impede performance of consensual sex especially among the young sexually active population. The wearer can always take it off or be forced to take it off for any purpose.

U.S. Pat. No. 5,368,050 issued Nov. 29, 1994 to J. P. Donelan discloses a rape prevention device including a belt adapted to encircle the waist of a wearer and a shield portion extending through the legs and crotch of the wearer from a rear region of the belt to the front region of the belt. The shield portion includes a plurality of shield segments adapted to cover the genitalia of the wearer. This invention while protectively covering only the genitalia of the wearer against rape, does not teach a method of urination or passing stool without unlocking and removing the device. Another shortcoming of this device is that it does not provide adequate protection against anal sex.

U.S. Pat. No. 5,613,251 issued Mar. 25, 1997 to C. N. Yandell discloses a device to prevent rape of a person wearing trousers or shorts in the form of locking and reinforced by an inter-lockable cut resistant belt system. This invention also concerns only specific category of rapists, such as the non aggressive type. Further more it does not give any protection against anal sex or rape.

The world is in an age when anal sex is now accepted as normal way of life. As the result anal rape has become an additional problem to people's social life. None of the referenced patents teaches a protective method against anal sex. Further more none of the referenced patents teaches a method which provides full protection to a person against genital and anal sex and resultant transmittal of venereal disease. Quite importantly, there is no invention which teaches method of enabling the wearer, especially sexually active youngsters to urinate and pass stool in a normal manner without unlocking and removing the protective cover especially when they are away from home.

THE INVENTION

The present invention relates to protective covers for sexual organs. More specifically, the device in this invention relates to a protective cover means which encloses and covers sexual organs such as the genitals and anal opening to prevent contacts with other sexual organs and the resultant discharges, thus to ultimately eliminate any chance of transmittal of and infection by venereal diseases as well as to minimize fear of rape. It is designed to function as security underwear.

OBJECTS OF THE INVENTION

1. The main object of this present invention is to stop contact between sexual organs and penetration thereof, which contact might cause transmittal of venereal diseases.

2. Another object of the invention is to provide protection against illicit sex, an act which might cause infection by transmittal of venereal diseases, as well as resultant psychological damages.

3. Still another object of the present invention is to prevent any external sexual discharges from coming in contact with unprotected sexual organs, thus stopping transmittal of venereal diseases carried by the said fluid.

4. Yet another object of the present invention is to enable the wearer of the device to use toilet freely without inconvenience and possible danger of having to take off the protective device.

5. Still another object of the present invention is to enable the wearer of the device to avoid carrying the key to the lock of the device thus minimizing any chance of committing consensual or illicit sex especially the young and the unmarried people.

6. Yet an additional object of this invention is to help minimization of multiple sex partnership, thus to indirectly discourage infection by venereal diseases outside two permanent sex partners.

7. It is also the purpose of this invention to empower those who are in constant fear of becoming victims of rape.

SUMMARY OF THE INVENTION

The protective cover device in this invention is to enclose, cover and protect the genital and the anal opening of a person against any chance of direct and indirect contact between the male and female sexual organs. The device has two major components, one to cover the genitalia and the other to cover the anal opening. Each major component fits over and covers the respective sexual part. The device is worn inside and along with underpants and locked on to a belt around the waist. No part or component of this new device can be easily cut or broken or removed without unlocking. Each major component of the protective cover has an opening which conforms with the shape and size of the respective body part. Each component can be worn with or without the other.

The opening of the cover for the female genitalia is wide enough to allow free urination but too narrow to allow an external object such as male genital to touch the female sexual organ. It has one inner cover and one channel type outer parts. The outer channel is superimposed over the inner cover. These inner and outer components are hinged to each other, thus assuming a general perspective view of a stapling machine. This arrangement is to make it double sure that no external object would be able to touch the sexual organ of a female. Additional flap covers to close the opening for urine passage is also provided to ensure prevention of flow of sexual discharges of one into the sexual organ of the another.

The protective cover for the anal opening is hinged on a frame positioned over and around the anal opening and functions by opening to the necessary extent only to allow stool passage. The hinging arrangement and the opening of the anal cover is such that it allows no external object to reach the anal opening. The hinged cover opens on its own or by hand when the underwear is pulled down or when it becomes necessary to use toilet.

Both major cover components are connected to each other at a crotch point between the thighs. The cover portion for the genitalia is fastened by strap means to the front side of the belt girdle on the waist and locked in place. Similarly the cover portion for the anal opening is fastened by means of another strap to the rear side of belt girdle. This way the protective cover is in position to protect the sexual organ of a person from rape and performance of illicit sex. Padding is provided to cover the skin of the wearer for possible protection against cuts, scratches or bruises. Additionally plurality of straps are provided to fasten the protective covers to the thighs. The size, the shape and weight of the security underwear is such that it is not noticeable on the wearer. The major achievement of this device is that it allows normal usage of toilet without having to take off the protective device. The wearer carries on her normal daily activities any where under any condition without any inconvenience or fear of rape. It therefore empowers women to be in full control of their daily lives.

BERIEF DESCRIPTION OF THE DRAWING

FIG. 7 is a perspective view of the invention showing the outer channel which is to be superimposed over the inner cover and hinged thereon to.

FIG. 8 is a side perspective view of the assembly of the preferred embodiment with the outer cover channel enclosing and superimposed over the inner cover.

FIG. 9 is a front end section view of the assembly of the two channels of the presently preferred embodiment in superimposed and closed position and showing added padding.

FIG. 10 is a side view of assembly of the two, inner cover and outer cover channel of the new invention hinged to each other with the outer channel in controlled open position, with added padding.

FIG. 11 is a perspective view of the inner cover of the present embodiment with flaps on each side of the urination slot positioned to cover and protect the opening for urine passage.

FIG. 12 is a plan view of anal area frame enclosing anal opening and its surrounding, provided with fastening straps at its two opposite upper and lower ends.

FIG. 13 is a perspective view of the present invention showing the protective cover for anal opening superimposed over and hinged to the anal area frame.

DETAIL DESCRIPTION OF THE PRESENTLY PREFERRED EMBODIMENT

Figure 1:
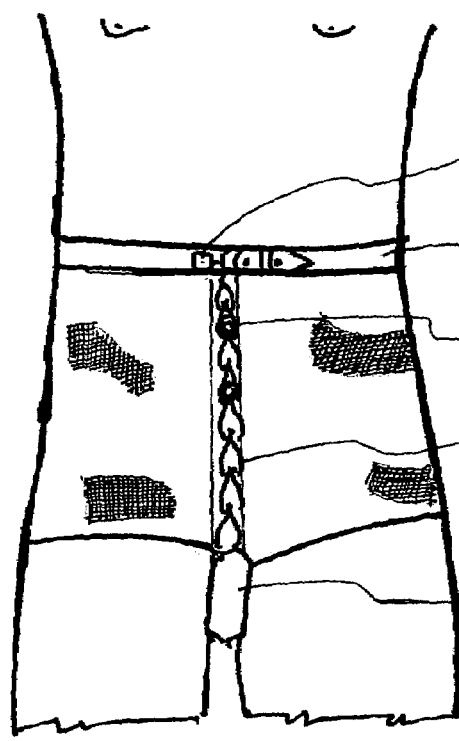
FIG. 1 is a perspective anterior view of the presently preferred exemplary embodiment of this invention worn over the genital and fastened to the belt of a female person.

These and other objects and advantages of the present invention will become more apparent and more readily appreciated from the following detailed description of the presently preferred exemplary embodiment, taken in conjunction with the accompanying drawing, of which:

As best illustrated in FIGS. 1, 3, 4, 6, 7 and 10 in the exemplary embodiment of the presently preferred invention, assembly of protective cover device 20 is worn over the genitalia of a female person. It comprises one inner cover 21 and one outer channel 22. The inner cover has an appropriate shape and size so that its walls 24 enclose and cover the genitalia and its immediate periphery to protect the organ from being touched by male genitalia. The walls also entrap the urine to direct it for normal flow and final discharge through urination slot 23 thus to prevent urine from splashing. An elongated urination slot 23 is provided in the center along the length of the inner cover. The slot is long and just wide enough to allow urine to pass through without impediment, but too narrow to allow a male genital to touch the female organ.

As illustrated in FIGS. 7, 8, 9 and 10 outer channel 22 has similar shape like the inner cover except that it is slightly wider and longer to fit over the inner cover when in closed position. The inner cover 21 and outer channel 22 are hinged to each other by means of hinge 25 at one of their ends like stapling machine. The hinge is lose enough to allow the outer channel to open and close freely on its own weight when the underwear is removed, or by the pressure from urine. The hinging may be spring loaded or resilient type if necessary. The hinged ends are to be positioned over the lower end of the female genital closer to the crotch. This allows the outer channel to open only at the other unhinged end during urination. This arrangement makes it impossible for male genital to make direct approach and get any closer to the female genital.

As best shown in FIG. 10 outer channel opening angle controller 26 is provided at the extreme end of the outer channel near to the hinging point 25. When the outer channel has to be opened to use toilet the angle controller allows the channel to open only to the desired extent by touching the end anchor 27 at the end of the inner cover and stops the outer channel from opening any further. The outer channel is long and narrow enough to act as an additional impediment to prevent the male genital from reaching and touching the female organ. Another important function of the outer channel is to receive the urine which passes through urination slot 23 of the inner cover. During urination the urine will flow out through the slot of the inner cover into the outer channel.

Figure 4:
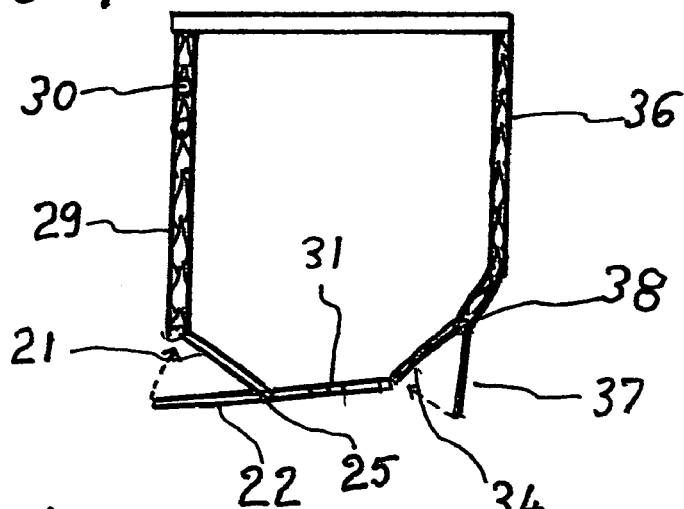
FIG. 4 is a side section view of the assembly of the protective cover provided with connector strap under the crotch and adjustable straps fastened to the wearer's belt at front and back.

As shown in FIG. 4 the outer channel 22 in an open position during urination slopes out and away from the genital and guides the urine outwardly for final discharge by force of gravity.

When urination is finished the underwear is pulled up over the protective cover thus forcing the outer channel to close over slot 23 of the inner cover channel. Alternatively spring loaded resilient hinging mechanism biased toward the inner would automatically close the slot of the inner even without the underpants being pulled up. The combination of the positioning, the point of hinging, the direction of opening, and the controlling mechanism of the extent of opening of the outer channel is such that it is virtually impossible for a male genital to touch the wearer's genitalia. When the outer channel covers the urination slot it would be impossible for any sexual fluid to flow into the enclosed genitalia, thus eliminating any chance of transmittal of venereal diseases via sexual contact.

As best illustrated in FIG. 11 flaps 28 are fastened to the inner cover along the length on both sides of the urination slot so as to cover the said slot 23. The said flaps are resilient type biased toward urination slot opening and should only be opened by force of urine and otherwise return to closing position. This method provides yet another additional protection in preventing any externally flowing sexual discharge from reaching the female genitalia. Such arrangement also makes it unnecessary to unlock the belt and pull down the underwear for urination, thus giving the wearer triple protection against any external object. As illustrated in FIGS. 1, and 4 adjustable vertical front side strap 29 is fastened to the top end of the presently preferred protective cover 20. Adjustment wholes 30 are provided along the upper end area of the adjustable strap. As best illustrated in FIGS. 1, 2, 3, and 4 connector strap 31, at one of its ends, is fastened to the bottom end of the inner cover 21 and at the other end fastened to frame 34 around anal opening 35. Lockable security belt 32 is provided to go around the wearer's waist. Locking device 33 is provided on the belt.

As best illustrated in FIGS. 3, 4, 5, 12 and 13, closed frame 34 is positioned over the ridges of the buttocks around anal opening 35. With the frame over the ridges of the buttocks, the anal opening region is open and free for stool passage.

Figure 2:
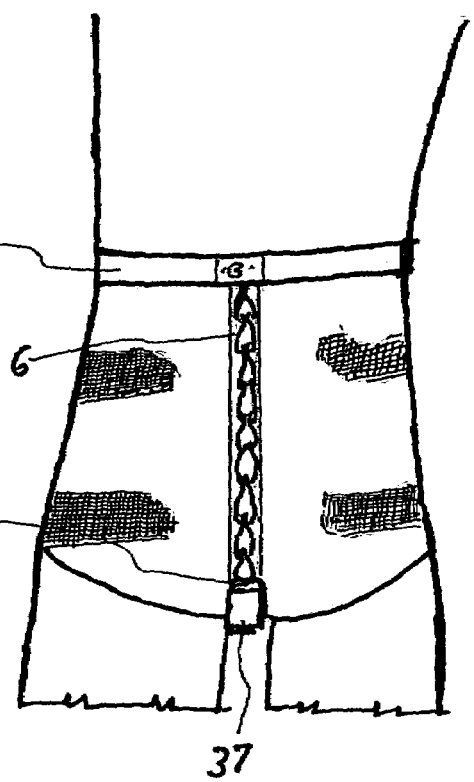
FIG. 2 is a perspective posterior view of the preferred embodiment worn over the anal and buttocks of a person and fastened to the rear side portion of the belt of a person.
Figure 3:
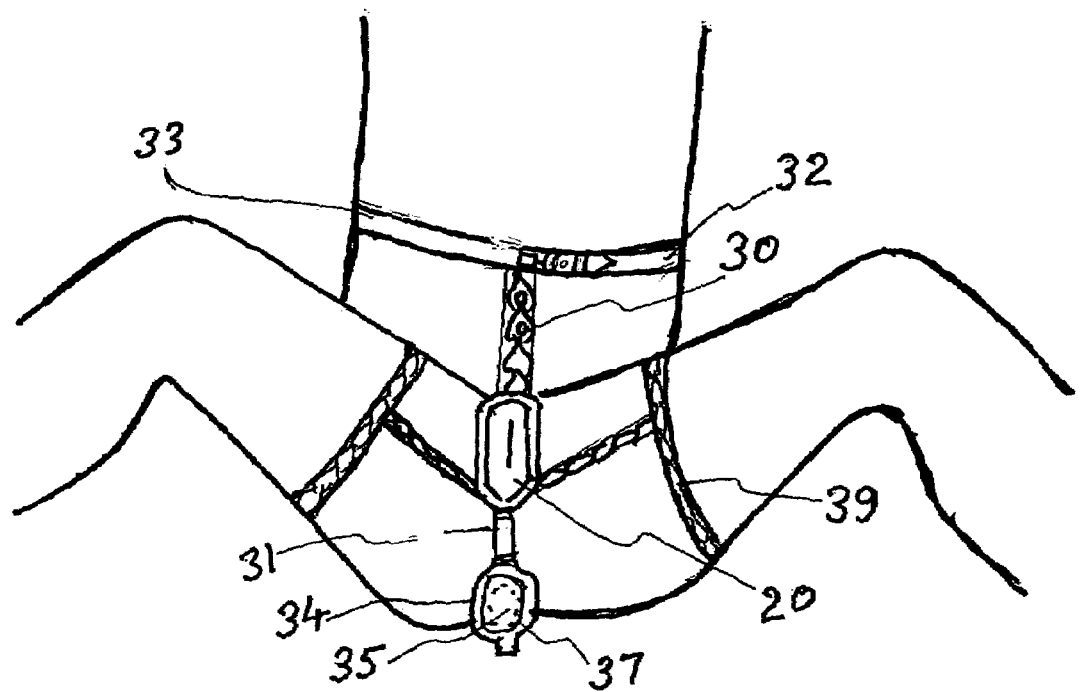
FIG. 3 is a plan view of the assembly of the invention device worn over the genital and anal opening of a female person.
Figure 5:
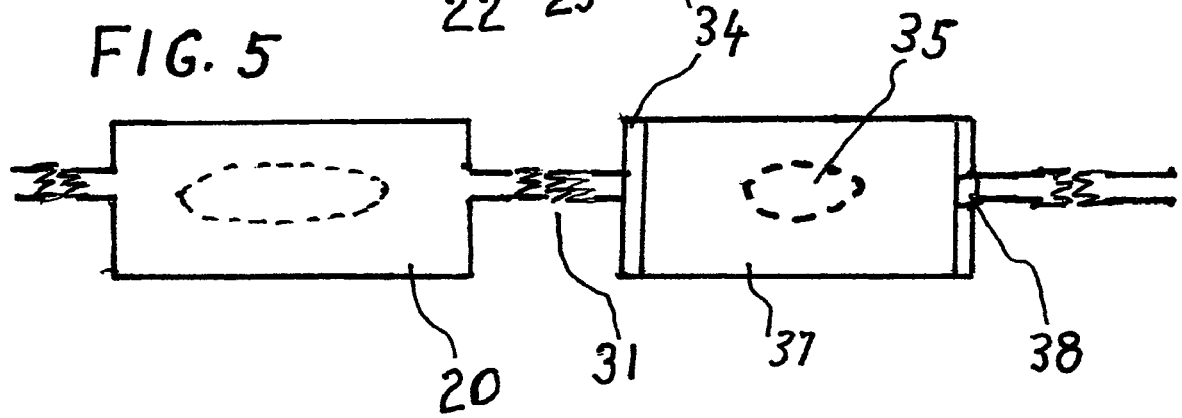
FIG. 5 is a plan view of the assembly of both covers for the genital and anal opening as normally fastened to each other.

As illustrated in FIGS. 2, 4, and 5 closed frame 34 at its lower end closer to the crotch is fastened to connector strap 31. The same closed frame 34 at its top end over the upper end of the buttocks is fastened to rear side vertical strap 36. Rear side vertical strap 36 at its upper end is fastened to the security steel belt 32 over the back side of the wearer's waist. When wearing the protective device for protection of female genital, the wearer fastens strap 36 to the back portion of security steel belt 32, positions closed frame 34 over the ridges of the buttocks around anal opening, ensures tight connection between closed anal frame 34 and inner cover 20 over the genital by means of connector strap 31, and pulls up the vertical front side strap 29, securely locks it on security steel belt 32 by means of locking device 33. Both front and back vertical straps can also be fastened to suspenders if necessary. Where suspenders are used to secure the device it should be the type of suspenders which cannot be pulled off over the head or over the shoulders. This requires a strap around the neck area to which the suspenders can be fastened. In such case the strap around the neck should be small or narrow enough to prevent easy removal over the head or shoulders. Both the suspenders and straps should be made of materials which are too hard to cut or break. To reinforce the security of the protective cover on the wearer, additional straps 37 can be provided around the periphery of the cover device and securely locked or permanently connected around the thighs. This arrangement is most preferred when the wearer wears the protective cover for female genitalia only. With this arrangement the wearer does not have to take off the device in order to use the toilet.

The arrangement as described above can only provide security against sexual contacts between female genitalia and male genitalia. However it does not provide protection against performance of anal sex. This problem can only be solved by providing yet another protective cover for anal opening.

As best illustrated in FIGS. 2, 3, 4, 5, 12 and 13 closed cover frame 34 for protective cover of anal opening, has appropriate size and shape conforming to that of the buttocks area and is designed to fit over the ridges of the buttocks. It encloses the middle space over the anal opening and leaves the anal opening uncovered. Protective cover means 38 over anal opening 35 is provided and designed to fit over cover frame 34 and fully cover and close the anal opening. The said cover 38 is hinged to cover frame 34 by means of hinge 39 at the top end of the anal cover frame close to the upper rear end of the buttocks. The hinging is such that the protective anal cover opens from the lower end close to the crotch. The hinging can be spring loaded or resilient type to ensure snap opening and closure of the cover when necessary. The extent of opening is controlled by using controlled or angle limiting devise similar to that of limiting embodiment for outer channel opening of the cover for the genital. The use of controlled hinging and direction of opening of anal cover together make it impossible to perform anal sex.

To ensure the desired full protection against anal sex, additional straps can be provided at appropriate points on the periphery of the anal cover frame to prevent any twisting of the cover system. These straps are to be tied around the thighs and securely locked in position.

With this arrangement both the genitalia and the anal opening are fully and securely protected. If for any reason the user wishes to wear only one of the protective covers all that is necessary is to remove the unwanted cover and securely fasten the straps to the remaining protective cover.

Figure 6:
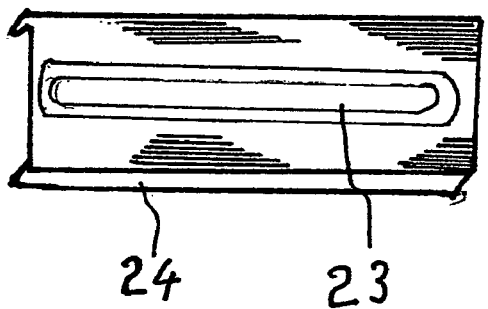
FIG. 6 is a perspective view of the present invention showing the inner cover channel for feminine genitalia with urination slot.
Figure 7:
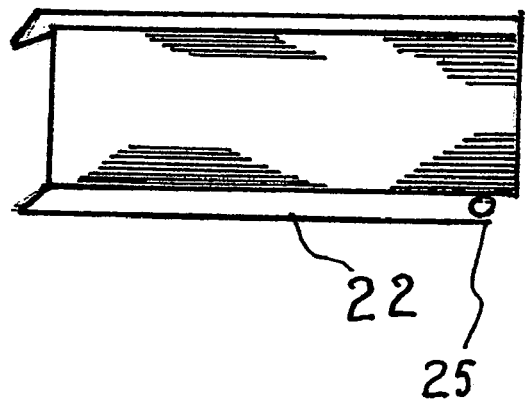

As best illustrated in FIGS. 6, 9, and 10 padding 40 is provided for all parts of the security underwear especially where it touches the wearer's skin. The padding ensures comfortable wearing against cuts or scratches of the skin. Alternatively, the whole device can be worn between two underpants; in which case the inner underpants must be modified by providing appropriate size holes directly over the genital and anal openings, and render the genital cover and the anal cover fully functional. To prevent easy removal of security underwear all components of the device, except the padding, should be made of materials which are too hard to cut or break or twist or bend. Once the whole assembly of the device in this invention, as described above is worn and locked on the body of the wearer, since it is not necessary to take off the security underwear in order to use toilet, especially in the case of young sexually active people, the key or the combination number of the lock should be kept away from the wearer. This way the would be sex offender cannot force the would be victim to unlock and undress and force himself on the victim. Even if consensual sex is allowed the key or the combination number should rather be obtained from the permanent partner or guardian. Although only a few exemplary embodiments of this invention have been described in detail above, those skilled in the art would readily appreciate that many modifications are possible in the exemplary embodiments without materially departing from the novel teachings and advantages of this invention. Accordingly, all such modifications are intended to be included within the scope of this application as defined in the following claims.

I claim:

1. Cover means for female sexual organs, where in said female sexual organs comprises female genitalia and anal opening, and said cover means for female sexual organs comprises cover means for female genitalia and cover means for anal opening, said cover means for female genitalia comprising:

one inner cover means, said inner cover means having appropriate shape and size which conforms with the shape and size of said female genitalia and the immediate periphery thereof, said inner cover means for said female genitalia having partially resilient and adjustable wall component, said inner cover means for female genitalia to provide closer and immediate protection for said female genitalia against attack from outside, said inner cover means for female genitalia having one first end and one second end, said inner cover means for female genitalia further comprising:

open means for urine passage, said open means for urine passage provided along the length of said inner cover means directly over the opening of said female genitalia, said open means for urine passage to allow and direct free flow of urine outwardly, frame means around anal opening, said frame means having shape and size which conforms with shape and size of buttocks around anal opening, said frame means around anal opening having open space at its general middle area, said open space being wide enough to allow stool to pass freely, said open space superimposed over said anal opening, said frame means around anal opening having one first end and one second end, said first end of said frame means around anal opening positioned over the upper end of buttocks and said second end of said frame means around anal opening positioned over the other end of said buttocks close to a crotch, means for connecting and fastening, said means for connecting and fastening having an elongated shape, said means for connecting and fastening being adjustable, said means for connecting and fastening positioned directly under said crotch, said means for connecting and fastening having one first end and one second end, said first end of said means for connecting and fastening connected and fastened to said first end of said inner cover means for female genitalia and said second end of said means for connecting and fastening connected and fastened to said second end of said frame means around anal opening, belt means around human torso, said belt means around human torso being lockable against forced removal, said belt means being adjustable, plurality of means for secure fastening, said means for secure fastening being adjustable, said means for secure fastening comprising at least one first fastening means and one second fastening means, said first fastening means deployed to connect, fasten and lock said inner cover means to front side portion of said belt means, and said second fastening means deployed to connect, fasten and lock said frame means around anal opening to back side portion of said belt means, means for locking, said means for locking to lock components of said cover means for female sexual organs to each other, said locking means further to lock components of said cover means for female sexual organs to said belt means around human torso, and all components of said cover means for female sexual organs to be made of materials very hard to cut or break, Such assembly, arrangement and deployment of said protective cover means to provide adequate security for female genitalia against unwanted and un allowed performance of sex, and therefore providing security against transmittal of venereal diseases through sexual organs.

2. Cover means for female sexual organs according to claim 1, where in said inner cover means further comprises channel means, said channel means designed to fittingly cover outer surface of said inner cover means, said channel means to receive urine flowing out through said open means for urine passage, said channel means for controlling urine splatter and further directing and discharging of urine, said channel means also to provide additional protection for said female genitalia against attack from male genitalia and any external object, said channel means having one first end and one second end, means for hinging, said means for hinging being resilient type, said means for hinging deployed to hinge said first end of said inner cover means to said first end of said channel means, said channel means capable to open and close at its unhinged said second end by force of urine.

3. Cover means for female sexual organs according to claim 2, where in said cover means for female sexual organs further comprises:

combination of said inner cover means, said channel means and said flap cover means, assembled, deployed and worn together to provide better protection for female genitalia.

4. Cover means for female sexual organs according to claim 3, where in said cover means for female sexual organs comprises combination of said inner cover means, said channel means, said flap cover means, and said anal cover means, assembled, deployed and worn together to provide comprehensive protection for female sexual organs.

5. Cover means for female sexual organs according to claim 2, where in said cover means for female sexual organs further comprises combination of said inner cover means, said channel means and said cover means for anal opening, assembled, deployed and worn together, to provide better protection for said female sexual organs.

6. Cover means for female sexual organs according to claim 1, wherein said inner cover means further comprises:

flap cover means, said flap cover means positioned along one or both sides of said opening means for urine passage so as to cover and close said opening means for urine passage, said flap cover means fastened to said inner cover means, said flap cover means being resilient type, said resilient flap cover means being biased so as to close said opening means for urine passage, said flap cover means capable to open by force of urine to allow urine discharge and capable to resiliently return to protective covering position and close said opening means for urine passage, said flap cover means, while in closed position, also being capable to stop sexual contact between male and female genitalias and thus stop sexual discharges from reaching either the male or female genitalia, therefore to stop transmittal of disease between the genitalias.

7. Cover means for female sexual organs according to claim 6, where in said cover means for female sexual organs comprises combination of said inner cover means, said flap cover means, and said cover means for anal opening, assembled, deployed and worn together, to provide better protection for female sexual organs.

8. Cover means for female sexual organs according to claim 1, where in said cover means for female sexual organs comprises:

cover means for anal opening, said cover means for anal opening comprising:

said frame means around anal opening, direct protective cover means for anal opening, said direct protective cover means for anal opening having wide enough surface to cover said anal opening and immediate periphery thereof, said direct protective cover means for anal opening positioned over said frame means around anal opening, means for hinging, said means for hinging deployed to hinge said direct protective cover means for anal opening to said frame means around anal opening, said means for hinging functioning by spring action, said spring action being biased so as to make said direct protective cover means close said anal opening when stool is not passing, said direct protective cover means for anal opening capable to open by force of stool, said direct protective cover means for anal opening to prevent performance of anal sex.

9. Cover means for female sexual organs, where in said female sexual organs comprise female genitalia and anal opening, and said cover means comprise cover means for female genitalia, and cover means for anal opening, said cover means for female genitalia further comprising:

one inner cover means, said inner cover means having appropriate shape and size which conforms with the shape and size of said female genitalia and the immediate periphery thereof, said inner cover means for female genitalia having partially resilient and adjustable wall component, said inner cover means for female genitalia to provide closer and immediate protection for said female genitalia against attack from outside, said inner cover means for female genitalia further comprising:

open means for urine passage, said open means for urine passage provided along the length of said inner cover means directly over the opening of said female genitalia, said open means for urine passage to allow free flow of urine outwardly, channel means, said channel means designed to fittingly cover outer surface of said inner cover means, said channel means to receive urine flowing out through said open means for urine passage, said channel means for controlling urine splatter and further directing and discharging of urine, said channel means also to provide additional protection for said female genitalia against attack from male genitalia and any external object, said channel means having one first end and one second end, means for hinging, said means for hinging being resilient type, said means for hinging deployed to hinge said first end of said channel means to said first end of said inner cover means, said channel means capable to open and close at its unhinged said second end by force of urine, means to control extent of opening, said means to control extent of opening deployed to control opening between said inner cover means and said channel means, said means to control extent of opening being adjustable, said inner cover means for female sexual organs further comprising:

flap cover means, said flap cover means positioned along one or both sides of said opening means for urine passage, said flap cover means fastened to said inner cover means, said flap cover means being resilient type, said resilient flap cover means being biased so as to overlap and cover and close said opening means for urine passage, said flap cover means capable to open by force of urine to allow urine discharge and capable to resiliently return to protective covering position and cover said opening means for urine passage, said flap cover means while in closed position, also being capable to stop sexual discharges from reaching either the male or female genitalia, therefore to stop transmittal of disease between said genitalias, cover means for anal opening, said cover means for anal opening further comprising:

frame means around anal opening, direct protective cover means for anal opening, said direct protective cover means for anal opening having wide enough surface to cover said anal opening and immediate periphery thereof, said direct protective cover means for anal opening positioned over said frame means around anal opening, means for hinging, said means for hinging deployed to hinge said direct protective cover means for anal opening to said frame means around anal opening, said means for hinging functioning by spring action, said spring action being biased so as to make said direct protective cover means close said anal opening when stool is not passing, said direct protective cover means for anal opening capable to open by force of stool, means to control extent of opening, said means to control extent of opening deployed to control extent of opening between said frame means and said direct protective cover means for anal opening, said direct protective cover means for anal opening to prevent performance of anal sex when in closed position, means for connecting and fastening, said means for connecting and fastening having an elongated shape, said means for connecting and fastening being adjustable, said means for connecting and fastening positioned directly under a crotch, said means for connecting and fastening having one first end and one second end, said first end of said means for connecting and fastening connected and fastened to said first end of said inner cover means for female genitalia, and said second end of said means for connecting and fastening connected and fastened to said second end of said frame means around anal opening, belt means around human torso, said belt means around human torso being lockable against forced removal, said belt means being adjustable, plurality of means for secure fastening, said means for secure fastening comprising at least one first secure fastening means for front side of human torso, and at least one second secure fastening means for back side of human torso, said first secure fastening means deployed to connect, fasten and lock said inner cover means to front side portion of said belt means, said second fastening means deployed to connect, fasten and lock said frame means around anal opening to back side portion of said belt means, said means for fastening being adjustable, means for locking, said means for locking deployed to lock components of said cover means for female sexual organs to each other, said locking means further to lock components of said cover means for female sexual organs to said belt means around human torso, and all components of said cover means for female sexual organs to be made of materials very hard to cut or break, such assembly, arrangement and deployment of components of said protective cover means for sexual organs to provide comprehensive security for female sexual organs against unwanted and un allowed performance of sex, and therefore providing security against rape, incest, child molestation and transmittal of venereal diseases through sexual organs and discharge thereof.

\* \* \* \* \*